United States Patent [19]

Plan et al.

[11] 3,992,367

[45] Nov. 16, 1976

[54] PROCESS FOR THE PREPARATION OF PURIFIED ALBUMIN BY THERMOCOAGULATION AND ALBUMIN OBTAINED BY SAID PROCESS

[75] Inventors: Robert A. M. Plan, Lyon; Jacques C. Liautaud, Limonest; Marie-France Makula, Lyon; Paule A. Gattel, Caluire; Jean F. Pla, Sainte-Foy-Les-Lyon; André J. M. Debrus, Lyon, all of France

[73] Assignee: Institut Merieux, Lyon, France

[22] Filed: July 3, 1973

[21] Appl. No.: 376,204

[30] Foreign Application Priority Data
July 5, 1972   France ............................ 72.24311

[52] U.S. Cl. ............................. 260/122; 260/112 B
[51] Int. Cl.² ............................................ C07G 7/00
[58] Field of Search ........................ 260/122, 112 B

[56] References Cited
UNITED STATES PATENTS

| | | | |
|---|---|---|---|
| 2,390,074 | 12/1945 | Cohn | 260/122 |
| 2,705,230 | 3/1955 | Reid | 260/122 |
| 2,761,810 | 9/1956 | Singer et al. | 260/112 B X |
| 2,765,299 | 10/1956 | Porsche et al. | 260/122 |
| 2,770,616 | 11/1956 | Cohn | 260/112 B |
| 2,958,628 | 11/1960 | Hink | 260/112 B X |
| 3,100,737 | 8/1963 | Auerswald et al. | 260/112 B X |
| 3,497,492 | 2/1970 | Buck et al. | 260/122 |
| 3,672,954 | 6/1972 | Grippa | 260/112 B X |

OTHER PUBLICATIONS

A Lab Manual of Analytical Methods of Protein Chemistry—vol. I, 1960, Alexander et al., pp. 6–9,11, 14–17, 67–68, 72.

Primary Examiner—Paul R. Michl
Attorney, Agent, or Firm—Cushman, Darby & Cushman

[57] ABSTRACT

Purified albumin is prepared from an albumin solution containing foreign or denatured proteins by heating the solution in the presence of caprylic acid at a pH of 4.8 – 5.25 at a temperature between 50° – 64° C. The amount of caprylic acid expressed in weight of sodium caprylate is between 15 – 30% by weight of the proteins in said solution.

17 Claims, 3 Drawing Figures

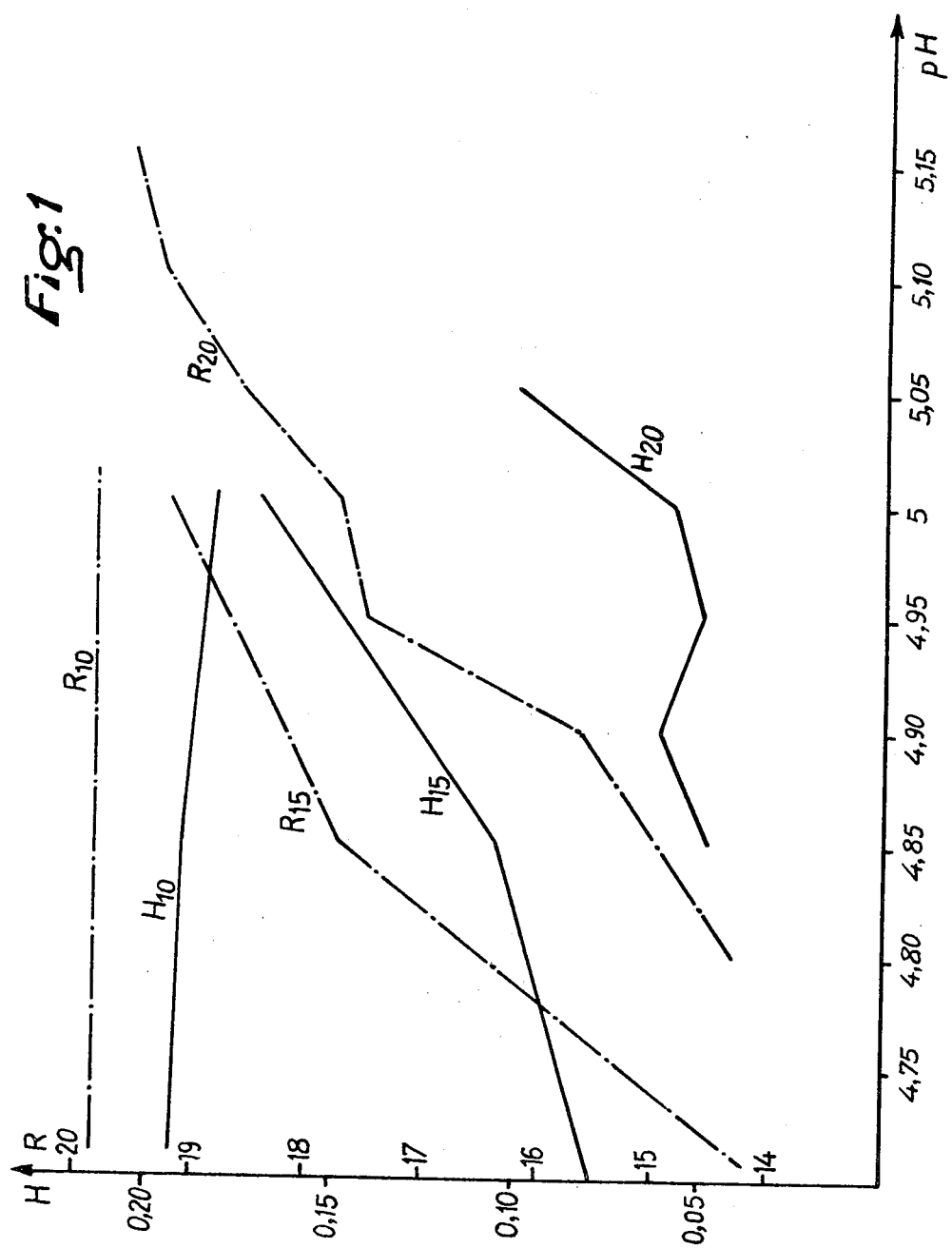

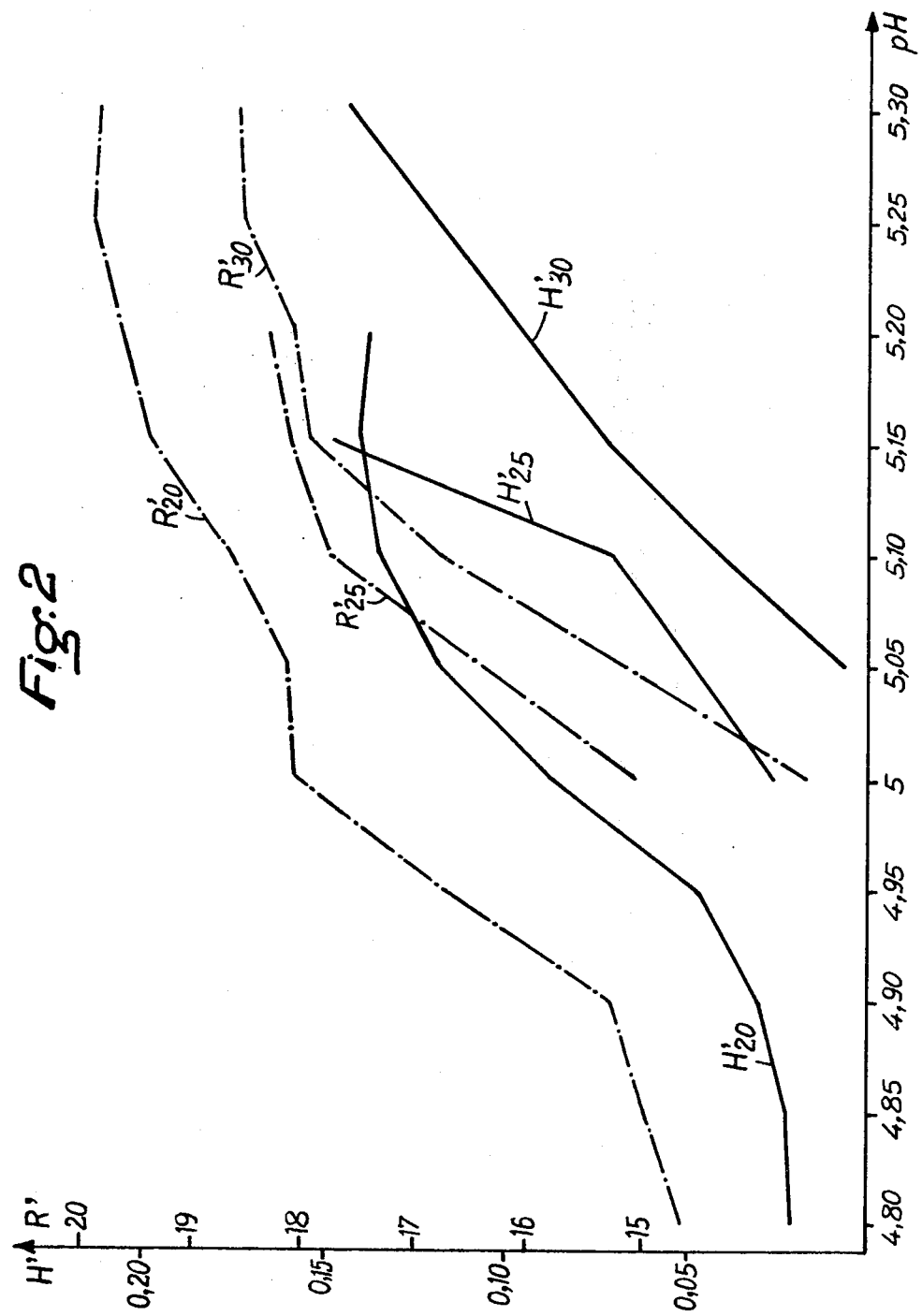

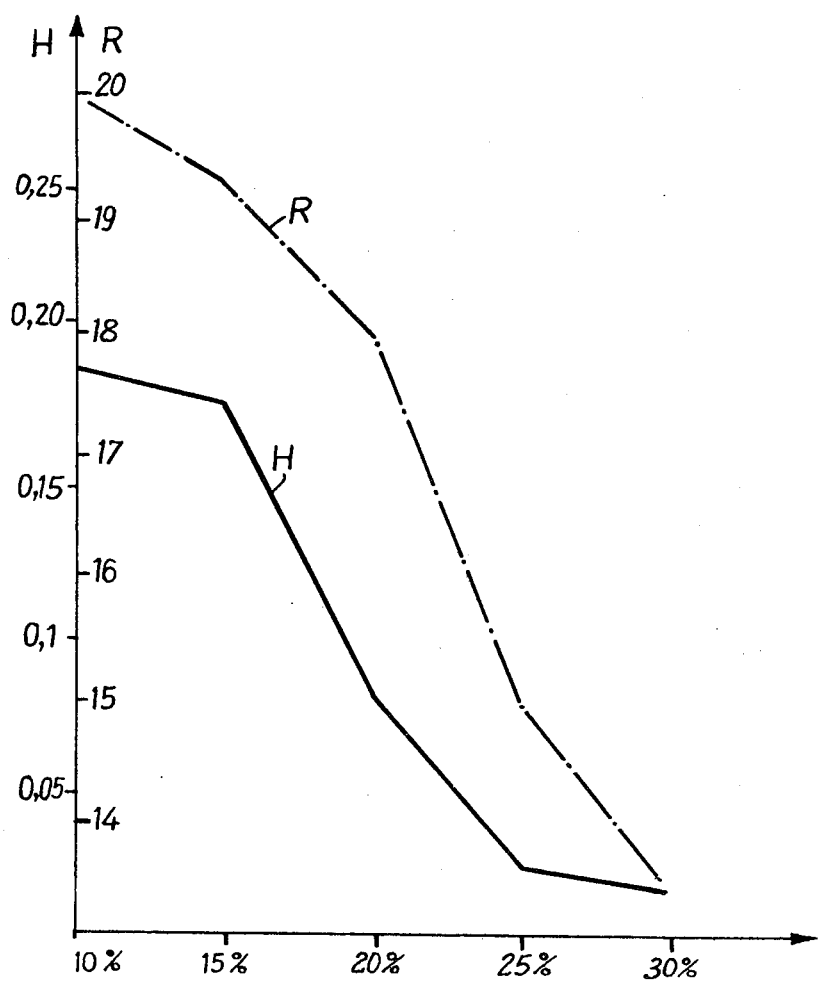

PROCESS FOR THE PREPARATION OF PURIFIED ALBUMIN BY THERMOCOAGULATION AND ALBUMIN OBTAINED BY SAID PROCESS

The present invention relates to a process for preparing purified albumin, particularly human albumin, and to the albumin obtained by said process.

The process of the present invention makes it particularly possible to prepare purified albumin not only from raw materials uncontaminated by hemoglobin, as for example, plasma, but also from materials contaminated by hemoglobin, as for example placentas, placental blood or generally any hemolyzed blood.

While the art already knows of processes for preparing purified albumin, none of these known processes, however, has made it possible, at least at a sufficiently economic cost, to produce large amounts of undenatured purified albumin, especially where the raw material is a material containing numerous impurities, and particularly hemoglobin.

The present invention, however, provides a process for preparing purified albumin, particularly human albumin, which is both simple and economical, and which makes it possible to prepare, industrially, large amounts of highly purified albumin from the most common sources.

The purified albumin obtained in accordance with this invention, when it is of human origin, can serve for the preparation of protein solutions that can be used as transfusion liquids, for example, in the treatment of shock, or in situations where there is a dangerous reduction in the amount of circulating blood.

This purified albumin of this invention is particularly well supported by the receiving organism and does not cause those reactions which often occur with standard albumin preparations.

Thus the present invention has for an object a process for preparing purified albumin, particularly human albumin, from an impure albumin solution containing foreign or denatured proteins, said process comprising thermocoagulating the undesired elements or impurities by heating said impure albumin solution in the presence of caprylic acid at a temperature between 52° C and 64° C, preferably between 56° C and 60° C. The thermocoagulation is preferably performed for a period at least equal to 30 minutes with an amount by weight of caprylic acid which, expressed in weight of sodium caprylate, is between 15% and 30% of the weight of the proteins of said solution, at a pH between 4.8 and 5.25.

Advantageously, the impure albumin solution used is preferably one in which the protein content is less than 50 grams per liter and, preferably, is about 20 grams per liter.

In a preferred embodiment, the caprylic acid is introduced in the form of sodium caprylate. However, it is also possible to introduce it in other forms, for example, in the form of the acid itself and not in the form of a salt. In this case, the caprylic acid content will be determined by a simple calculation from the preceding values which correspond to the case where the caprylic acid is introduced in the form of sodium caprylate.

Generally, the pH of the impure albumin solution is selected so as to be greater as the proportion of the caprylate content relative to the protein content is increased. For example, when the caprylate content is equal to 15% of the protein content, the pH will, preferably, be of the order of 4.85 to 4.95, while for a caprylate content equal to 20% of the protein content, the most favorable pH will be between 4.95 and 5.05. For a 25% caprylate content, the pH will preferably be close to 5.1, while for a 30% caprylate content, the pH will, advantageously, be of the order of 5.15.

The thermocoagulation thus performed makes it possible to eliminate a great part of the hemoglobin and to precipitate the denatured albumin and the foreign proteins.

Where the solution to be purified has been obtained from a plasmatic origin, the process of the present invention makes it possible directly to obtain a directly usable purified albumin.

Where the source of the solution to be purified is one which is more contaminated by foreign bodies, for example, placenta, placental blood or hemolyzed blood, advantageously the thermocoagulation procedure is preceded by at least one of the following operations: (a) eliminating a major part of the hemoglobin, (b) eliminating enzymes, such as alkaline phosphatases by the precipitation of proteins with an acid such as trichloroacetic acid or polyphosphoric acids, and (c) eliminating group substances.

The elimination of the hemoglobin can advantageously be carried out in the presence of an ethanol concentration less than 60%, with the addition of a halogenated hydrocarbon such as chloroform. It can, however, also be carried out by the addition of a halogenated hydrocarbon, without alcohol or by other known processes.

The elimination of enzymes, such as the phosphatases, is carried out preferably after the hemoglobin elimination stage, and is preferably performed in the presence of an ethanol concentration less than 60%, with the addition of trichloroacetic acid. The acid concentration can be between $3 \times 10^{-2}$ and $10 \times 10^{-2}$ M/liter, preferably, $4.2 \times 10^{-2}$ M/liter, the acid being added to the protein solution at a temperature below 0° C and, preferably, between −5° and −10° C, until essentially total precipitation of the proteins is achieved. In addition to eliminating enzymes, this stage also makes it particularly possible to concentrate the amount of albumin in solution, because the albumin precipitates.

In certain cases, it is possible to replace the precipitation with trichloroacetic acid by precipitation with polyphosphoric acid.

The elimination of group substances is preferably carried out with an ethanol concentration greater than 55%, for example, about 75%, with a protein concentration preferably less than or equal to 10 g/liter, and by adding trichloroacetic acid to the solution at a temperature below 0°, for example, between −5° and −10° C. The amount of trichloroacetic acid can advantageously be of the order of $8 \times 10^{-2}$ M/liter. The precipitate obtained is discarded, thereby eliminating the group substances.

This group substances elimination stage also makes it possible to remove alkaline phosphatases so that the preceding stage of elimination of phosphatases can, if desired, be omitted and replaced by a simple protein concentration operation.

The present invention also has for an object albumin prepared in accordance with the process described above, which albumin has properties which are practically identical with those of original organic albumin. Thus the albumin produced in accordance with the present invention can be used for the treatment of ailments and particularly for the treatment of human ailments.

Other advantages and characteristics of the invention will be apparent from the following description, and from the accompanying drawing wherein:

FIG. 1 represents the curves of rate of hemoglobin and yield of proteins as a function of the pH for a first lot of albumin, FIG. 2 represents the curves for another lot, and FIG. 3 represents the curves of albumin yield and hemoglobin level as a function of the caprylate content for a same pH value.

Referring to FIG. 1, there are shown, as a function of the pH, plotted on the abscissa, the curves R representing protein yield and curves H representing residual hemoglobin level after the caprylate treatment of this invention. A batch of placental human albumin used to develop these curves initially contained 20 g/l of protein, principally albumin, and a little less than 0.2 in hemoglobin level (optical density of a 1% solution). Curves R thus represent the weight in grams per liter of protein, essentially albumin, which remains in solution after thermocoagulation with caprylate. Coloring H of the albumin was evaluated photometrically by a simple reading on a Beckman spectrophotometer, at 403 $\mu$, after having adjusted the protein content of the solution to 10 g per liter.

As can be seen from FIG. 1, for an amount of caprylate equal to 2 g per liter, i.e., 10% of the initial weight of protein, curves $R_{10}$ and $H_{10}$, which correspond to this caprylate content, are approximately horizontal. This means that practically no protein precipitates and that the hemoglobin level remains essentially constant. Thus for a caprylate content equal to 10%, thermocoagulation in accordance with the present invention does not produce the desired results.

However, when the caprylate content is increased to 15% by weight relative to the protein weight, i.e., 3 g/l of caprylate, the result achieved is represented by curves $R_{15}$ and $H_{15}$. It can be thus seen that the protein yield is higher as the pH increases but that the hemoglobin level evolves in the same way. Still, for a pH close to 4.8, it is possible to cause the hemoglobin level to drop by more than half, provided a loss of about 4 g/l of protein is accepted. In this connection, it should be noted that the purity of the albumin obtained by the process according to the present invention is relatively independent of the protein yield, because foreign proteins and the denatured fraction of albumin precipitate first. Therefore, it suffices to have a complete precipitate to be certain of having eliminated almost all the undesirable proteins. Continuation of the precipitation eliminates a part of the pure albumin and therefore causes the yield to drop.

When the caprylate content is equal to 20% of the initial protein content, i.e., 4 g/l, the results are shown on curves $R_{20}$ and $H_{20}$. It can be seen that for a pH close to 4.95 to 5, there is still retained a considerable amount of purified albumin, while the hemoglobin content is clearly reduced.

Referring now to FIG. 2, curves R' and H', respectively, represent the protein content and hemoglobin level after thermocoagulation on a second batch of placental albumin treated in accordance with the present invention.

For a caprylate content equal to 20% of the initial protein weight of the solution to be thermocoagulated, i.e. a caprylate content of 20 g/l, a protein yield curve $R_{20}'$ is obtained, which corresponds approximately to curve $R_{20}$. Curve $H_{20}'$ follows a trend which is also close to curve $H_{20}$ and there again the most favorable zone is located in the vicinity of a pH equal to 5.

If the caprylate content is increased, referring to curves $R_{25}'$ and $H_{25}'$, to a caprylate content of 25%, it is found that a favorable zone is present for a pH close to 5.1.

Finally, for a 30% caprylate content, the results shown in curves $R_{30}$ and $H_{30}$ show that the optimum pH is located in the vicinity of 5.15. Actually, it is in this pH zone that a considerable lowering of the hemoglobin level is obtained for an albumin yield that is still suitable.

FIG. 3 illustrates the behavior for a batch of thermocoagulated albumin as a function of the percentage of caprylate, at the same pH equal to 5. Thermocoagulation is carried out at a temperature of 60° C for a period of 1 hour. It can be seen that the protein yield, and also the hemoglobin level, drop when the caprylate content increases, but that an optimum is reached for a caprylate content of 20%. Actually, for this value, the yield is equal to 90%, which means that only 10% of the proteins have precipitated, while the hemoglobin level has gone from about 0.20 to a value between 0.1 and 0.05.

The following example is given to illustrate the present invention.

For about 7 tons of placenta, there is prepared, in a conventional manner, a supernatant by precipitation of the globulin content with ethanol.

1. Elimination of hemoglobin

To the alcoholic supernatant containing about 25% ethanol and containing about 58 g of protein per kg of placenta chloroform is added so that the total volume of about 17,000 liters contains 0.6% chloroform. The pH is then adjusted to a value between 6.0 and 6.1.

The supernatant is maintained, under these conditions, at a temperature of about 24° C, whereby a precipitate is formed which is then separated and discarded.

The volume of supernatant is thereby reduced to about 16,000 liters and the protein yield is about 8 g/kilo. The greatest part of the hemoglobin content has thus been eliminated.

2. Elimination of enzymes

To the supernatant of 16,000 liters previously obtained containing about 25% ethanol and after lowering the temperature thereof to −8° C, trichloroacetic acid is added to obtain a concentration of $4.2 \times 10^{-2}$ M/liter. The amount of protein is about 4 g/liter.

There is thus obtained a precipitate of about 1000 kg, while the supernatant having a volume of about 15,000 liters, is discarded. For this purpose, hermetic centrifuges are used preferably with continuous ejection of the precipitate. Thus the alkaline photphatases and other enzymes, such as transaminases, are eliminated or denatured.

The resulting precipitate is then redissolved in dilute NaOH to a neutral pH and the volume is adjusted to 1400 liters with water.

3. Clarification

To this redissolved precipitate, there is added silica powder (aerosil) to obtain an aerosil concentration of about 0.2%. Thus a precipitate of about 50 kg is formed which is rejected by centrifuging. The clarified supernatant solution corresponds to a protein yield of about 6.5 g per kg.

4. Elimination of group substances

Group substances are principally made up of polysaccharides of walls of erythrocytes which are dissolved at the time of hemolysis and which must be eliminated.

The clarified solution from step 3 above is diluted with a mixture of ethanol and trichloroacetic acid, the final strength of the alcohol being about 75%, and the strength of the trichloroacetic acid being about $8 \times 10^{-2}$ M/liter. The protein content is about 10 g/liter. The temperature being kept at about $-7°$ C, a precipitate of about 10 kg is formed which is rejected and the group substances are eliminated. This stage also completes the elimination of possible residual enzymes.

The supernatant which contains about 8 g/l of proteins is then filtered and the pH is adjusted to a value between 6.5 and 7, the temperature always being maintained between $-5°$ and $-10°$ C. The albumin precipitate which is thus formed is then centrifuged, yielding about 140 kg of precipitate. The supernatant is discarded.

5. Purification of the albumin

The precipitate resulting from step 4 is redissolved in water to form a volume of about 280 liters, the protein yield being 5 g/kg.

After dialysis against distilled water to eliminate the alcohol, the level of proteins is adjusted to 20 g/liter. Then sodium caprylate, in a concentration of $2.41 \times 10^{-2}$ M/liter (4 g/liter) is added to the solution, and the pH is adjusted to a value between 5.0 and 5.05, for example, with an acetic buffering solution.

This solution is kept at 60° C for about 1 hour.

The remaining proteins, except albumin, are thus coagulated and are rejected in a precipitate with the last traces of hemoglobin and the denatured fraction of albumin. Essentially only pure albumin remains in solution.

The resulting supernatant is then brought to about 1750 liters and is filtered. The diluted albumin solution is then concentrated by adjusting 40% ethanol to a pH between 4.8 and 4.9 at a temperature of the order of $-8°$ C. A precipitate is then formed which is collected, then redissolved, this new solution then being dialyzed and then treated on alumina gel. Subsequently, the solution is concentrated under vacuum and filtered under sterile conditions to provide about 95 liters of an essentially pure concentrated solution of albumin of about 200 g/liter. At this final stage, the protein yield is about 2.7 g/kg. The coloring of the solution is comparable to that of most good solutions of plasmatic origin.

The invention described with this example is of course able to be the object of numerous variants. Thus, certain preliminary stages can be omitted or again replaced by similar conventional stages. Further, the order in which the preliminary stages are conducted can be modified.

The human albumin thus prepared is free of group substances and placental alkaline phosphatases, and does not have a hypotensive effect on the perfused dog. Its slight hemoglobin level makes it comparable and even superior to most albumins of plasmatic origin.

This albumin can be used for therapeutic purposes in man without drawbacks and meets all the criteria established for albumin control.

What is claimed is:

1. Process of preparation of purified albumin substantially free of hemoglobin and foreign or denatured proteins from an impure albumin solution to be purified from which a major part of the hemoglobin has been eliminated, said impure albumin solution containing said foreign or denatured proteins and remaining traces of hemoglobin and having a protein content less than 50 grams per liter, comprising thermocoagulating said foreign or denatured proteins and said remaining traces of hemoglobin by heating said solution to be purified in the presence of a member selected from the group consisting of caprylic acid and a salt thereof at a pH between 4.8 and 5.25, the amount of said member, expressed in weight of sodium caprylate, being between 15% and 30% of the weight of proteins in said solution to be purified, said heating being carried out at a temperature between 50° C and 64° C and wherein the pH of the impure albumin solution is selected so as to be the greater as the proportion of the caprylate content relative to the protein content is increased.

2. Process according to claim 1, wherein the thermocoagulation is carried out for a period equal to at least thirty minutes.

3. Process according to claim 1, wherein the thermocoagulation is carried out at a temperature between 56° C and 60° C.

4. Process according to claim 1 wherein the protein content of said solution to be purified is about 20 g/liter.

5. Process according to claim 1 wherein the thermocoagulation is carried out in the presence of sodium caprylate.

6. Process according to claim 1 wherein the pH is selected from the group consisting of (a) between 4.85 to 4.95 when the proportion of caprylate content relative to the protein content is equal to 15%, (b) between 4.95 and 5.05 when said proportion is equal to 20%; (c) about 5.1 when said proportion is equal to 25%; and (d) about 5.15 when said proportion is equal to 30%.

7. Process according to claim 1 wherein said solution to be purified originates from placenta, placental blood or hemolyzed blood, and wherein the thermocoagulation is preceded by at least one step selected from the group consisting of (a) eliminating enzymes by precipitation of proteins with an acid and (b) eliminating the group substances.

8. Process according to claim 1, wherein elimination of said major part of the hemoglobin is carried out in the presence of an ethanol concentration less than 60% with addition of a halogenated hydrocarbon.

9. Process according to claim 7, wherein elimination of enzymes is carried out in the presence of an ethanol concentration less than 60% with addition of trichloroacetic acid.

10. Process according to claim 9, characterized by the fact that the trichloroacetic acid concentration is between $3 \times 10^{-2}$ and $10 \times 10^{-2}$ M/liter.

11. Process according to claim 7 wherein elimination of group substances is carried out in the presence of an ethanol concentration greater than 55% by adding trichloroacetic acid at a temperature below 0°.

12. Process according to claim 8 which also includes clarifying the solution by contacting the same with a silica gel.

13. Process according to claim 1 which includes, subsequent to the thermocoagulation, separating the precipitate formed by centrifuging and filtering the supernatant.

14. Process according to claim 1 which includes, subsequent to the thermocoagulation, concentrating the albumin solution by precipitation by the addition of ethanol thereto.

15. Process according to claim 14, wherein the resulting precipitate is redissolved, the solution then being dialyzed and then treated on alumina gel.

16. Process according to claim 15, wherein the solution, subsequent to treatment on alumina gel, is concentrated under vacuum and filtered under sterile conditions.

17. Process according to claim 16 wherein the thermocoagulation is preceded by the steps consisting of (a) eliminating a major part of the hemoglobin, (b) eliminating the alkaline phosphatases in the presence of ethanol at a concentration of less than 60% with addition of trichloroacetic acid, at a temperature below 0° C, until essentially total precipitation of the proteins is achieved, and (c) adding trichloroacetic acid in the presence of ethanol at a concentration of more than 55%, with a protein concentration less than or equal to 10 g/liter, at a temperature below 0° C, and discarding the precipitate thus formed, thereby eliminating the group substances.

\* \* \* \* \*

UNITED STATES PATENT OFFICE
CERTIFICATE OF CORRECTION

Patent No. 3,992,367  Dated November 16, 1976

Inventor(s) Robert Plan et al

It is certified that error appears in the above-identified patent and that said Letters Patent are hereby corrected as shown below:

In the Abstract:

Line 4, "$50°-64°C$" should read --$52°-64°C$--.

In the Claims:

Claim 1, (Col. 6, line 18) "$50°C$ and $64°C$" should read --$52°C$ and $64°C$--.

Signed and Sealed this

Nineteenth Day of April 1977

[SEAL]

Attest:

RUTH C. MASON  
*Attesting Officer*

C. MARSHALL DANN  
*Commissioner of Patents and Trademarks*